(12) United States Patent
Woo

(10) Patent No.: US 6,603,033 B2
(45) Date of Patent: Aug. 5, 2003

(54) ORGANOTITANIUM PRECURSORS FOR CHEMICAL VAPOR DEPOSITION AND MANUFACTURING METHOD THEREOF

(75) Inventor: Kyoungja Woo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/052,130

(22) Filed: Jan. 16, 2002

(65) Prior Publication Data

US 2003/0040638 A1 Feb. 27, 2003

(30) Foreign Application Priority Data

Jan. 19, 2001 (KR) .......................... 2001-3137

(51) Int. Cl.[7] .............. C07F 7/28; C23C 16/00
(52) U.S. Cl. .............. 556/40; 556/54; 427/585; 427/593
(58) Field of Search ............ 556/40, 54; 427/585, 427/593

(56) References Cited

U.S. PATENT DOCUMENTS 3,856,839 A * 12/1974 Smith et al. ............. 556/40

FOREIGN PATENT DOCUMENTS

| JP | 10-114781 | 5/1998 |
|---|---|---|
| JP | 11-255784 | 9/1999 |
| WO | 00/37712 | 6/2000 |

OTHER PUBLICATIONS

Jung–Hyun Lee et al. Chemical Vapor Deposition of Barium Strontium Titanate Films with Direct Liquid Injection of Single–Mixture Solution. *Journal of the Electrochemical Society*, vol. 146(10), pp. 3783–3787, Feb. 1, 1999.

Jung–Hyun Lee et al. "Chemical Vapor Deposition of Barium Strontium Titanate Thin Films Using Direct Liquid Injection of a Single Cocktail Solution with Ba (methd)$_2$, Sr (methd)$_2$, and Ti (MPD) (tmhd)$_2$". *J. Mater. Res.*, vol. 14, No., 10, Oct. 1999.

* cited by examiner

*Primary Examiner*—Porfirio Nazario-Gonzalez
(74) *Attorney, Agent, or Firm*—Pennie & Edmonds LLP

(57) ABSTRACT

The invention comprises an organotitanium precursor formed from a β-ketoester and a titanium glycolate, and dimer precursors formed from a reaction of the above organotitanium precursor with alcohol, which are used as sources of titanium dioxide for metal-organic chemical vapor deposition (MOCVD).

6 Claims, 3 Drawing Sheets

ORGANOTITANIUM PRECURSORS FOR CHEMICAL VAPOR DEPOSITION AND MANUFACTURING METHOD THEREOF

BACKGROUND OF THE INVENTION

1. Field of the Invention

The present invention relates to organotitanium precursors for use as source materials for titanium dioxide in metal-organic chemical vapor deposition and methods for making such precursors. More particularly, the invention is an organotitanium precursor made of a β-ketoester and a titanium glycolate, and dimer precursors derived from a reaction of the above organotitanium precursor and alcohol.

2. Description of the Related Art

Volatile organotitanium precursors are generally used as source materials for fabrication of thin films of ferroelectrics and paraelectrics such as PZT and BST by metal-organic chemical vapor deposition (MOCVD) as these precursors are constitutents of titanium dioxide thin film. Known titanium tetraalkoxide precursors are so sensitive to the atmosphere and moisture that they are easily decomposed or oligomerized. There is therefore a problem in the art as this sensitivity detracts from the very properties sought, namely, the volatile properties of the precursors.

Accordingly, in order to overcome this drawback, $Ti(OPr^i)_2(tmhd)_2$ (wherein, $OPr^i$ is isopropoxide, and tmhd is 2,2,6,6-tetramethyl heptanedionate) was developed in which two diketone compounds substitute for two alkoxides. However, because $Ti(OPr^i)_2(tmhd)_2$ is also decomposed or oligomerized by a disproportionation reaction during its use, the problem of volatility was not resolved. Additionally, the decomposition reaction of this precursor proceeds in a complicated two steps or more process wherein a thin film is obtained only at a high temperature above 460° C. Further, humps and haziness appear on the surface of the deposited thin film, and the surface has protrusions which are not smooth, as shown in WO 00/37712, *J. Electrochem. Soc.,* 146(10) 3783–3787 1999.

In 1998, the Japanese Asahi Denka company developed $Ti(mpd)$ $(tmhd)_2$ (wherein, mpd is 2-methyl-2,4-pentanediolate). Compared with $Ti(OPr^i)2(tmhd)_2$, the decomposition reaction of $Ti(mpd)$ $(tmhd)_2$ is simpler and the drawback of thermal decomposition or oligomerization during its use, was resolved.

However, for depositing a titanium dioxide thin film using $Ti(mpd)$ $(tmhd)_2$, the temperature of the substrate has to be maintained at 480° C. or higher to maintain a sufficient deposition rate allowing a deposition of thin film having a constant titanium composition ratio. If $Ti(mpd)$ $(tmhd)_2$ is used with traditional DRAM technologies allowing a temperature application of at most 470° C., a Ti-deficient thin film can be deposited.

If $Ti(mpd)$ $(tmhd)_2$ is used to manufacture a thin film having a composition ratio of barium and strontium to titanium of 1:1 in the BST film, the deposition rate of this titanium precursor is low, and there is a need to maintain a composition ratio of barium to strontium to titanium precursor at 1:1:8 in a mixed solution of $Ti(mpd)(tmhd)_2$, barium, and strontium precursors. Accordingly, there is a serious waste of titanium precursor. Further, $Ti(mpd)(tmhd)_2$ precursor is a brown colored glass-like solid, and is sold in the form of solution dissolved in a solvent. Therefore, it is not easy to separate the pure precursor of solid phase and deal with it, as disclosed in Japanese Laid-Open Publication Nos. 11-255784 and 10-114781, and *J. Mater. Res.,* 14(10), 3988–3994 1999.

SUMMARY OF THE INVENTION

It is an object of the present invention to provide organotitanium precursors which are highly adaptive and efficient as source materials for MOCVD, and manufacturing methods for the inventive organotitanium precursors.

Another object of the present invention is to provide organotitanium precursors having superior stability and volatility which can be used in uncomplicated decomposition reactions on substrates with a high deposition rate at low temperatures such as 470° C. or lower, and providing an easy dealing, such that they are very useful as source materials for MOCVD.

The organotitanium precursor of the present invention is of Formula 1 as follows,

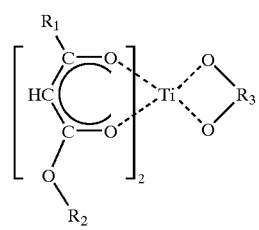

Formula 1 where $R_1$ and $R_2$ can each be a straight- or branched chain alkyl group each having 1–8 carbon atoms, a cycloalkyl group, a phenyl group or a benzyl group, and $R_3$ is a straight- or branched chain alkylene group having 2–13 carbon atoms.

The di-nuclear organotitanium precursor of the present invention has Formula 2 as follows,

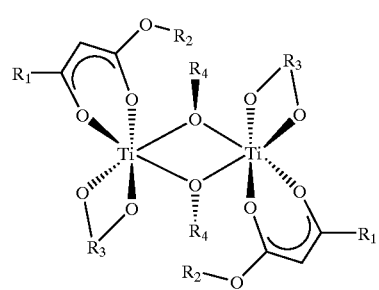

Formula 2 where $R_1$ and $R_2$ can each be a straight- or branched chain alkyl group each having 1–8 carbon atoms, a cycloalkyl group, a phenyl group or a benzyl group, $R_3$ is a straight-or branched chain alkylene group having 2–13 carbon atoms, and $R_4$ is a straight chain alkyl group having 1–8 carbon atoms.

The method for making the organotitanium precursor of Formula 1 comprises reacting a titanium tetraalkoxide, $Ti(OR)_4$, wherein R is a straight- or branched chain alkyl group having 1–4 carbon atoms, with a diol of Formula 3. Next, a β-ketoester of Formula 4 is added to the resulting reaction intermediate to form a reaction product. All unnecessary by-product ROH is removed. If a solvent was used in the initial step whereby reaction intermediate is formed from $Ti(OR)_4$, such solvents are also removed with unnecessary by-product ROH. The reaction product is then distilled under reduced pressure. The structure of Formula 3 is HO—$R_3$—OH, where $R_3$ is a straight- or branched chain alkylene group having 2–13 carbon atoms, and Formula 4 has the following structure, Formula 4

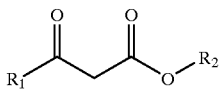

where $R_1$ and $R_2$ can each be a straight- or branched chain alkyl group each having 1–8 carbon atoms, a cycloalkyl group, a phenyl group or a benzyl group.

The di-nuclear organotitanium precursor of Formula 2 is made with a process comprising the steps of reacting a $Ti(OR)_4$, wherein R is a straight- or branched chain alkyl group having 1–4 carbon atoms, with a diol of Formula 3. To the resulting reaction intermediate is added a β-ketoester of Formula 4 to form a mono-nuclear reaction product. All unnecessary by-product ROH is removed. If a solvent was used in the initial step whereby reaction intermediate is formed from $Ti(OR)_4$, such solvents are also removed with unnecessary by-product ROH. The mono-nuclear reaction product is then distilled under reduced pressure. Either before or after the distilling step, an alcohol, $R_4OH$, where $R_4$ is a straight chain alkyl group having 1–8 carbon atoms, can be added to the mono-nuclear reaction product, thereby yielding di-nuclear reaction product.

DETAILED DESCRIPTION OF THE PREFERRED EMBODIMENTS

Figure 1:
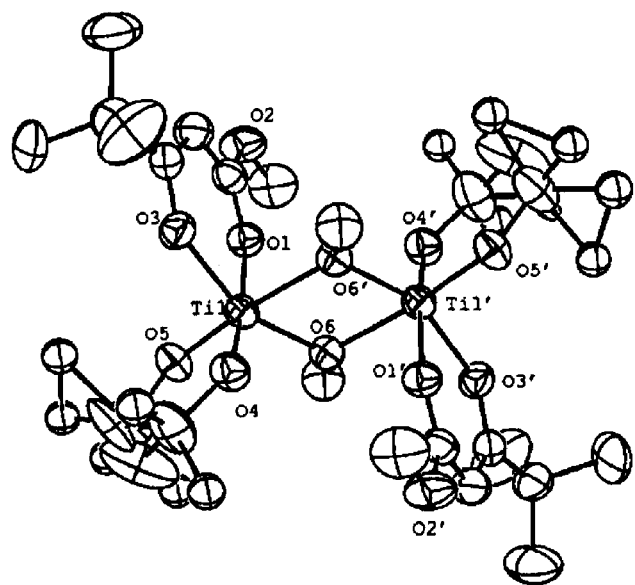
FIG. 1 is a molecular structure by an X-ray crystallographic analysis of a chemical compound manufactured with embodiment five of the present invention.

Preferred embodiments of the present invention will now be described in detail.

In order to form an organotitanium precursor which is stable in normal atmosphere and easy to work with, there should be a satisfactory structure in which the six coordination sites of titanium are saturated. Also, in order for the organotitanium precursor to have superior volatility, an asymmetric (not symmetrical) organic ligand is preferred.

It is well known that manufacturing a BST thin film with conventional $Ti(OPr^i)_2(tmhd)_2$ and $Ti(mpd)(tmhd)_2$ precursors cause Ti-deficiency and raises deposition temperature because titanium is bound too strongly to tmhd.

There is structural similarity between a structure where a proton is dissociated from a β-diketone and that proton is bound to two oxygen atoms of the β-diketonate and a structure where titanium coordinates with two oxygen atoms of a β-diketonate. Therefore, if a chelating organic ligand having a proton dissociation constant which is smaller than that of the β-diketone is selected to synthesize the organotitanium precursor, bond strength with titanium is weakened, and as a result, deposition at even lower temperatures may be possible and deposition rate thereof may be higher.

Considering these points, the present invention adopts β-ketoester breaking symmetry and having a proton dissociation constant one hundred times smaller than that of the diketone that is a symmetric organic ligand, and makes mono-nuclear organotitanium precursors. Additionally, these precursors are treated with alcohol to make di-nuclear precursors. The mono- and di-nuclear precursors show higher deposition rates and have better stability and volatility.

Accordingly, the present invention provides novel organotitanium precursors of Formulas 1 and 2 which are volatile and stable in normal atmosphere and have high deposition rates.

Formula 1:

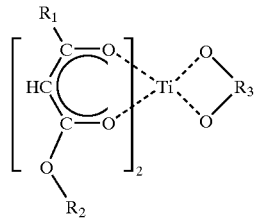

where $R_1$ and $R_2$ are each selected from the group consisting of a straight- or branched chain alkyl group each having 1–8 carbon atoms, a cycloalkyl group, a phenyl group and a benzyl group, and $R_3$ is a straight- or branched chain alkylene group having 2–13 carbon atoms.

Formula 2:

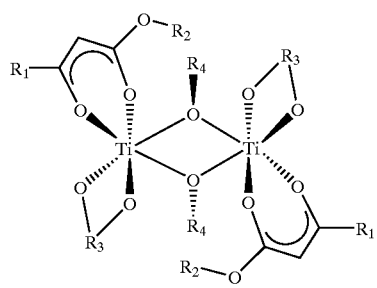

where $R_1$ and $R_2$ are each selected from a group consisting of a straight- or branched chain alkyl group each having 1–8 carbon atoms, a cycloalkyl group, a phenyl group and a benzyl group, $R_3$ is a straight- or branched chain alkylene group having 2–13 carbon atoms, and $R_4$ is a straight chain alkyl group having 1–8 carbon atoms.

The present method makes the organotitanium precursor of Formula 1 in the form of a liquid having high viscosity. The method comprises, reacting titanium tetraalkoxide, $Ti(OR)_4$ wherein R is a straight- or branched chain alkyl group having 1–4 carbon atoms, with a diol of Formula 3. A β-ketoester of Formula 4 is then added to the resulting reaction intermediate to form a reaction product. All unnecessary by-product ROH is removed along with any solvent used in the initial step whereby reaction intermediate is formed from Ti(OR)$_4$. The reaction product is then distilled under reduced pressure.

The present method for making the organotitanium precursor of Formula 2 in a white solid state, further comprises the step of adding an alcohol expressed as R$_4$OH wherein R$_4$ is a straight chain alkyl group having 1–8 carbon atoms, to the reaction product before or after the distilling step under reduced pressure, as noted in the above method for making the organotitanium precursor of Formula 1.

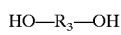　　　　　　　　　　　　　　Formula 3 where R$_3$ is a straight- or branched chain alkylene group having 2–13 carbon atoms.

Formula 4:

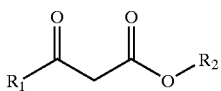

where R$_1$ and R$_2$ are each a straight- or branched chain alkyl group having 1–8 carbon atoms, a cycloalkyl group, a phenyl group or a benzyl group.

Provided below are details on making mono-nuclear organotitanium precursors from β-ketoester and titanium glycolate, and di-nuclear precursors wherein an alkoxide is bridged to the mono-nuclear precursors.

In Formulas 1 and 2, straight- or branched chain alkyl groups having 1–8 carbon atoms include methyl, ethyl, propyl, isopropyl, n-butyl, isobutyl, t-butyl, n-penthyl 2-pentyl, 3-pentyl, neopentyl, n-hexyl, 2-hexyl, 3-hexyl isoheptyl, isooctyl, 2-octyl, 3-octyl, 2-ethylhexyl, and the like, and a cycloalkyl group includes a cyclohexyl group.

Also, in Formulas 1 and 2, straight- or branched chain alkylene group having 2–13 carbon atoms is provided by glycol (diol). Examples of the glycol include ethane-diol, 1,3-propanediol, 1,3-dimethyl-1,3-propanediol, 2,2-dimethyl 1,3-propanediol, 2-methyl-2-ethyl-1,3-propanediol, 2,2-diethyl-1,3-propanediol, 2-ethyl-2-butyl-1, 3-propane-diol 1-methyl-1,3-propanediol, 2-methyl-1,3-pro-panediol, and functional and structural equivalents. Among the aforementioned examples, 1,3-propanediol and alkyl derivatives thereof are especially preferred because they further enhance effects of the present invention.

In Formula 2, straight- or branched chain alkyl groups having 1–8 carbon atoms are provided by alcohols. Examples of alcohols include primary alcohols such as methanol, ethanol, n-propanol, n-butanol, n-pentanol, n-hexanol, n-heptanol, and n-nonanol. It is believed that secondary alcohols having 3 or more carbon atoms cannot form a bridged bond due to their steric hindrance.

More specific examples of the organotitanium precursor of the present invention are chemical compounds of the following Formulas 5–12. However, these compounds are illustrated for purposes of example and are in no way intended to limit the present invention.

Formula 5:

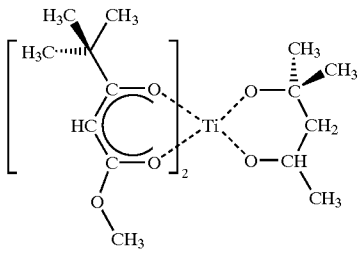

Ti (mpd) (mdop)$_2$ (abbreviation)

Formula 6:

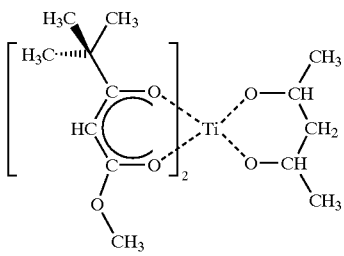

Ti (pd) (mdop)$_2$ (abbreviation)

Formula 7:

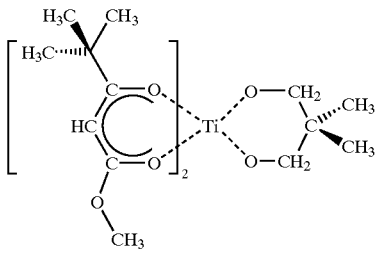

Ti (npg) (Mdop)$_2$ (abbreviation)

Formula 8:

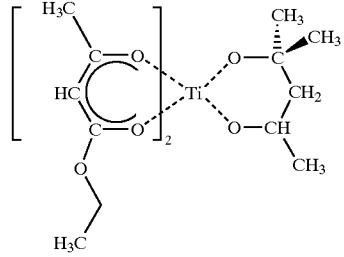

Ti (mpd) (etac)$_2$ (abbreviation)

Formula 9:

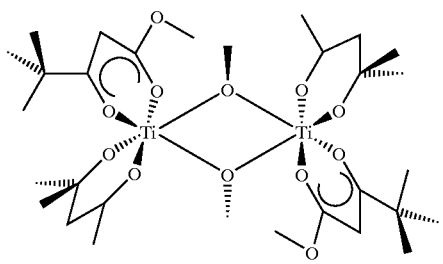

[Ti (mpd) (mdop) (OMe)]$_2$ (abbreviation)

Formula 10:

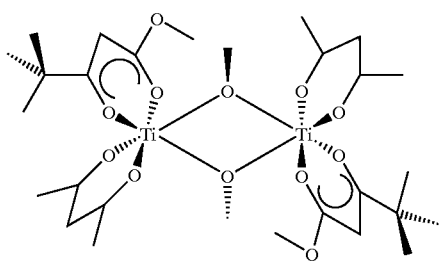

[Ti (pd) (mdop) (OMe)]$_2$ (abbreviation)

Formula 11:

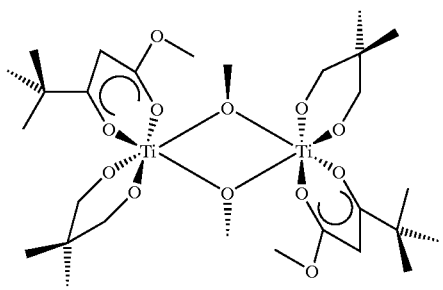

[Ti (npg) (mdop) (OMe)]$_2$ (abbreviation)

Formula 12:

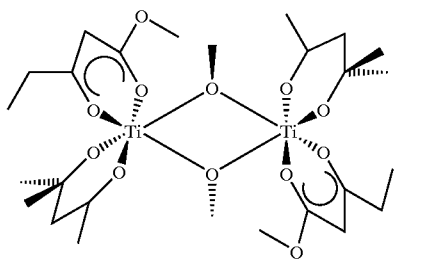

[Ti (mpd) (etac) (OMe)]$_2$ (abbreviation)

In the method for manufacturing organotitanium precursors in accordance with the present invention, the titanium tetraalkoxide may be reacted with the glycol and β-ketoester without any solvent. It is more desirable that the titanium tetraalkoxide is dissolved in a solvent to uniformly dissolve the reactants, especially a solvent dehydrated and distilled according to known methods to form a solvent system. The solution is then reacted with the glycol and the β-ketoester.

The solvent is preferably an aliphatic or aromatic hydrocarbon solvent. As solvents, alcohols or amines that react with the reactants are not preferred. Further, in order to effectively remove the solvent used to dissolve the titanium tetaalkoxide and the alcohol generated as an unnecessary by-product during making of the organotitanium precursor, it is desirable to choose a solvent which can make an azeotropic mixture with the by-product at a low boiling point.

A di-nuclear organotitanium precursor bridged by alkoxide is manufactured according to the above-noted method for making the mono-nuclear organotitanium precursor with the added step of adding an excess amount of alcohol to the mono-nuclear organotitanium precursor before or after the distilling step, thereby obtaining the di-nuclear organotitanium precursor in white solid state. The added alcohol plays a dual role as both a solvent and a reagent.

The process for making the mono- and di-nuclear organotitanium precursors of the present invention are as follows.

First, 1 mol of commercially available titanium tetraalkoxide is reacted with glycol in a molar ratio of 1:1, and then reacted with β-ketoester in a molar ratio of 1:2. The solvent and by-products are then removed and the reaction product is distilled under reduced pressure. The mono-nuclear organotitanium precursor of Formula 1 is obtained in yellow liquid state having high viscosity. The di-nuclear organotitanium precursor of Formula 2 is obtained as white solid product by adding alcohols to the organotitanium precursor of Formula 1 before or after the distilling step.

The present method for making mono-nuclear precursor utilizes the characteristic property of mono-alkoxides which are easily substituted by di-alkoxides and by β-ketoester anion due to chelating effect. Substantially similar results are obtained by stirring the reactions at room temperature for 16 hours or more, or by refluxing the reactions above 80° C. for one hour.

[Embodiment 1: Manufacturing Ti(mpd) (mdop)$_2$ of Formula 5]

First, 4.72 mL (16.0 mmol) of titanium tetra-isopropoxide was dissolved in 16 mL of dehydrated and distilled hexane solvent under nitrogen atmosphere.

Next, 2.04 mL of 2-methyl-2,4-pentanediol was added to the resulting solution and stirred for one hour at room temperature, and then 5.11 mL of methyl 2,2-dimethyl-3-oxopentanote was added and refluxed for one hour.

Subsequently, the hexane solvent and a by-product, i.e. isopropanol, were distilled/removed and further distilled in reduced pressure thereby obtaining 6.48 g (84.7%) of the compound of Formula 5 as a yellow liquid with high viscosity. The compound of Formula 5 was analyzed and the result was placed in Table 1. NMR(600 MHz, in $C_6D_6$) δppm; 5.314(2H), 5.175 and 4.983(1H), 3.249(6H), 2.022 (1H), 1.830(1H), 1.600 and 1.433(3H), 1.225–1.214(24H). FT-IR (solution in benzene); 3112, 2961, 2926, 2892, 2866, 1629, 1612, 1590, 1534, 1508, 1456, 1400, 1357, 1280, 1228, 1193, 1150, 1077, 973, 939, 892 $cm^{-1}$.

[Embodiment 2: Manufacturing Ti (pd) (mdop)$_2$ of Formula 6]

First, 2.36 mL (8.00 mmol) of titanium tetraisopropoxide was dissolved in 8 mL of dehydrated and distilled hexane solvent under nitrogen atmosphere.

Next, 0.88 mL of 2,4-pentanediol was added to the resulting solution and stirred for one hour at room-temperature, and then 2.56 mL of methyl 2,2-dimethyl-3-oxopentanoate was added and refluxed for one hour.

Thereafter, the hexane solvent and a by-product isopropanol, were distilled to remove and further distilled in reduced pressure thereby obtaining 2.95 g (79.4%) of the compound of Formula 6 as a yellow liquid with high viscosity. The compound of Formula 6 was analyzed and the result was placed in Table 1. NMR(600 MHz, in $C_6D_6$) δ ppm; 5.337(2H), 5.09–4.76(2H), 3.279(6H), 1.983–1.691 (2H), 1.208–1.158(24H). FT-IR (solution in benzene); 3233, 3116, 2965, 2922, 2862, 2275, 1633, 1612, 1590, 1534, 1512, 1452, 1400, 1361, 1331, 1279, 1228, 1150, 1129, 1098, 978, 956, 887 $cm^{-1}$.

[Embodiment 3: Manufacturing Ti(npg) (mdop)$_2$ of Formula 7]

First, 0.833 g of neopentylglycol was prepared in a flask inside a glove box under argon atmosphere and then it was dissolved in 12 mL of dehydrated and distilled hexane under nitrogen atmosphere.

Next, 2.36 mL of titanium tetraisopropoxide was added to the resulting solution and reacted for one hour at room temperature, and then 2.56 mL of methyl 2,2-dimethyl-3-oxopentanoate was added and stirred for sixteen hours at room temperature.

Thereafter, a very small amount of solid was removed by filtering the solution and the filtrate was concentrated and kept in a refrigerator thereby obtaining 1.47 g (39.6%) of the compound of Formula 7 as a white solid. The compound of Formula 7 was analyzed and the result was placed in Table 1. FT-IR (solution in benzene); 2952, 2923, 2899, 2867, 2826, 2675, 1631, 1533, 1513, 1456, 1387, 1354, 1277, 1228, 1146, 1089, 1007, 971 $cm^{-1}$.

[Embodiment 4: Manufacturing Ti(mpd) (etac)$_2$ of Formula 8]

First, 2.36 mL of titanium tetraisopropoxide was dissolved in 8 mL of dehydrated and distilled hexane under nitrogen atmosphere.

Next, 1.02 mL of 2-methyl-2,4-pentanediol was added to the resulting solution and was subject to reaction for one hour at room temperature, and then 2.04 mL of ethyl acetoacetate was added to the solution, and they were stirred for sixteen hours.

Thereafter, the hexane solvent and a by-product isopropanol, were distilled to remove and further distilled under reduced pressure thereby obtaining 2.73 g (80.8%) of the compound of Formula 8 as a yellow liquid. The compound of Formula 8 was analyzed and the result was placed in Table 1. FT-IR (solution in benzene); 3112, 2974, 2931, 2857, 1633, 1607, 1573, 1530, 1443, 1409, 1370, 1280, 1215, 1172, 1150, 1060, 1012, 969, 939, 891 $cm^{-1}$.

[Embodiment 5: Manufacturing [Ti (mpd) (mdop) (OMe)]$_2$ of Formula 9]

Using the same process as in the first embodiment, dehydrated and distilled methanol was added to a reaction product, which was not yet distilled under reduced pressure, thereby obtaining white solid. This solid was filtered, washed with cold methanol, and dried more than five hours under a vacuum state to thereby yield 3.48 g of the compound of Formula 9. The compound of Formula 9 was analyzed and the result was placed in Table 1. A single crystal was grown from the above filtrate and was examined by the X-ray crystallographic analysis and the result was shown in FIG. 1.

According to the X-ray crystallographic analysis for the compound of Formula 9, the compound is a dimer molecule in which each methoxide is bridged to two titaniums and three methyl groups of mpd ligand exist as a disordered structure.

Figure 2:
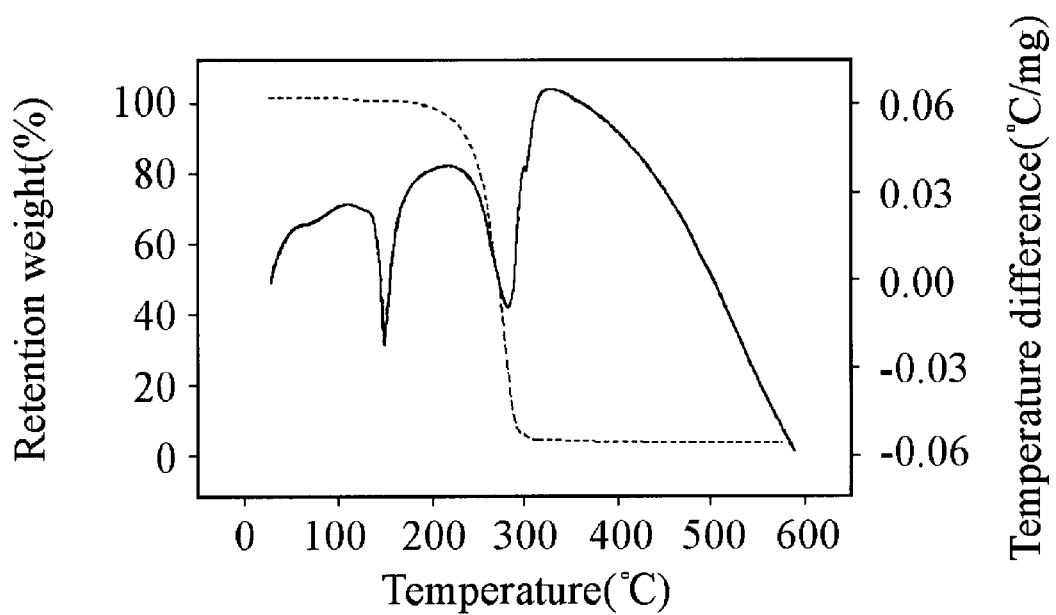
FIG. 2 is a graph illustrating data from a TG/DT analysis of the chemical compound depicted in FIG. 1.

The result of a thermal analysis for the above compound of Formula 9 is shown in FIG. 2. This compound is considered as a high quality organotitanium precursor since it has excellent volatility, is decomposed by simple process and its decomposition is completed at as low temperature as below 300° C. FT-IR (solution in benzene); 2970, 2922, 2862, 2820, 1622, 1598, 1532, 1514, 1454, 1400, 1358, 1281, 1226, 1190, 1155, 1076, 1047, 1023, 968, 945 $cm^{-1}$.

[Embodiment 6: Manufacturing [Ti(pd)(mdop)(OMe) ]$_2$ Of Formula 10]

Using the same process as in the second embodiment, dehydrated and distilled methanol is added to a reaction product, which is not yet distilled under reduced pressure, thereby obtaining white solid. During the above reaction, the reaction scale is two times bigger than that of the second embodiment. The solid was filtered, washed with cold methanol, and dried more than five hours under a vacuum state to thereby yield 3.08 g of the compound of Formula 10. The compound of Formula 10 was analyzed and the result was placed in Table 1. FT-IR (solution in benzene); 3055, 2964, 2928, 2864, 1631, 1613, 1592, 1533, 1515, 1448, 1396, 1355, 1281, 1227, 1154, 1126, 1096, 1050, 1021, 975, 952 $cm^{-1}$.

[Embodiment 7: Manufacturing [Ti (npg) (mdop) (OMe)]$_2$ of Formula 11]

Using the same process as in the third embodiment, dehydrated and distilled methanol was added to a reaction product after concentration of the filtrate, thereby obtaining white solid. During the above reaction, the reaction scale was two times bigger than that of the third embodiment. This solid was filtered, washed with cold methanol, and dried more than five hours under a vacuum state to thereby yield 3.56 g of the compound of Formula 11. The compound of Formula 11 was analyzed and the result was placed in Table 1. FT-IR (solution in benzene); 3055, 2955, 2909, 2856, 2829, 1631, 1613, 1595, 1533, 1514, 1451, 1398, 1281, 1227, 1154, 1126, 1092, 1048, 1020, 975 $cm^{-1}$.

[Embodiment 8: Manufacturing [Ti(mpd)(etac)(OMe)]$_2$ of Formula 12]

Using the same process as in the fourth embodiment, dehydrated and distilled methanol was added to a reaction product, which is not yet distilled under reduced pressure, thereby obtaining white solid. During the above reaction, the reaction scale was two times bigger than that of the fourth embodiment. This solid was filtered, washed with cold methanol, and dried more than five hours under a vacuum state to thereby yield 2.06 g of the compound of Formula 12 The compound of Formula 12 was analyzed and the result was placed in Table 1. FT-IR (solution in benzene); 3045, 2973, 2928, 1623, 1605, 1523, 1361, 1281, 1172, 1145, 1037, 965, 938 $cm^{-1}$.

Yield of the white solids in the embodiments 3, 5 to 8 increased by keeping the concentrated filtrate in a refrigerator.

[Embodiment 9]

Figure 3:
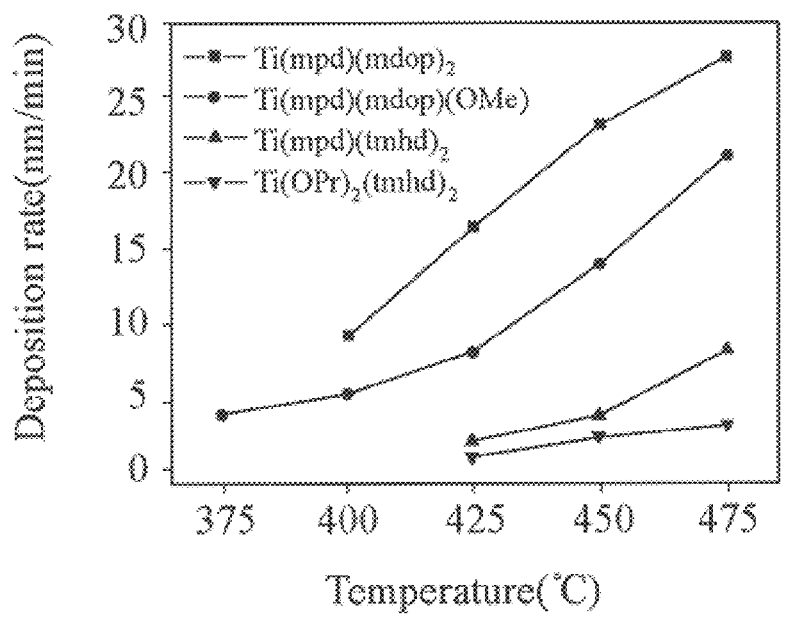
FIG. 3 is a graph showing results from comparing deposition rates of the respective organotitanium precursors tested in embodiment nine of the present invention.

Each thin film was manufactured by using compounds of Formulas 5 and 9, Ti(OPr$^i$)$_2$(tmhd)$_2$ and Ti(mpd) (tmhd)$_2$ as the respective precursor in accordance with the LS-MOCVD (Liquid Source Metal-Organic Chemical Vapor Deposition), and deposition rates were compared (FIG. 3).

The thin film was manufactured under the following conditions, in which:

CVD equipment were of the substrate-heating type CVD equipment and a direct liquid injection system, which are manufactured by the inventors of the present invention;

Reaction gas is oxygen ($O_2$);

Carrier gas is argon (Ar);

Substrate is Pt/TiN/SiO$_2$/Si;

Temperature of substrate is 375–475° C.;

Temperature of evaporation is 280° C.;

Concentration of precursors is 0.08 mol/L; and

Solvent for the compound of formulas 5 and 9 is toulene, and solvent for $Ti(OPr^i)_2(tmhd)_2$ and $Ti(mpd)(tmhd)_2$ is n-butylacetate.

TABLE 1

| Compound (Formula No.) | Calculated Molecular Weight | Observed Molecular Weight (Mass spectra) | Melting Point (° C.) | Shape |
|---|---|---|---|---|
| 5 | 478 | 478 | | yellow liquid |
| 6 | 464 | 464 | | Yellow liquid |
| 7 | 464 | 464 | 150, decomposition | White solid |
| 8 | 422 | 422 | | Yellow liquid |
| 9 | 704 | 673 ($M-OCH_3^-$) | 130–134 | white solid |
| 10 | 676 | 645 ($M-OCH_3^-$) | 93–97 | white solid |
| 11 | 676 | 645 ($M-OCH_3^-$) | 180, decomposition | white solid |
| 12 | 648 | 617 ($M-OCH_3^-$) | 85–88 | white solid |

| Compound (Formula No.) | Weight Decrease-Starting Point (TGA) (° C.) | Evaporation/Sublimation Condition | |
|---|---|---|---|
| | | Temp. (° C.) | Pressure (mmHg) |
| 5 | | 140–150 | 0.35–0.40 |
| 6 | | 140–150 | 0.25 |
| 7 | | Decomposition starts at 150° C. | |
| 8 | | 140–150 | 1.0 |
| 9 | 183 | 140–150 | 0.03 |
| 10 | 125 | 110–120 | 0.02 |
| 11 | | Decomposition starts at 180° C. | |
| 12 | | 80–90 | 0.05 |

As illustrated in FIG. 3, it is noted that deposition rates of the compounds of Formulas 5 and 9 according to the present invention are remarkably higher than those of the conventional $Ti(OPr^i)_2(tmhd)_2$ and $Ti(mpd)(tmhd)_2$.

Figure 4:
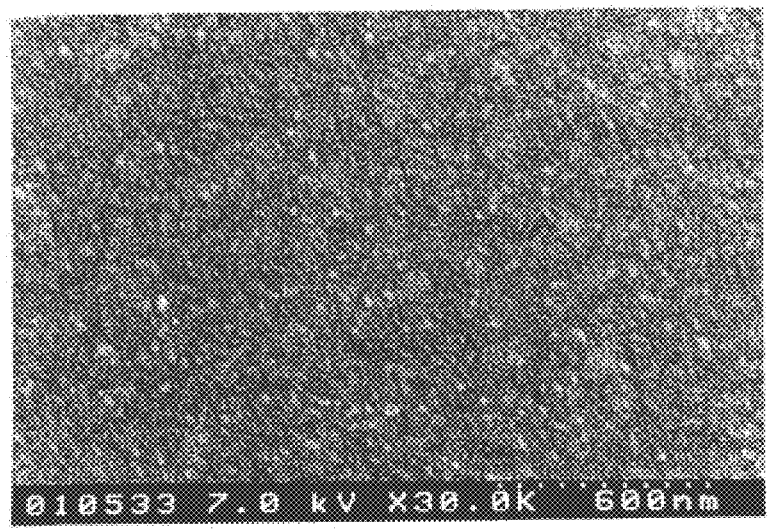
FIG. 4 is a scanning electron microscopy (SEM) micrograph showing a plain-view surface shape of a thin film deposited using the organotitanium precursor of formula 9 at 425° C. in accordance with the ninth embodiment.
Figure 5:
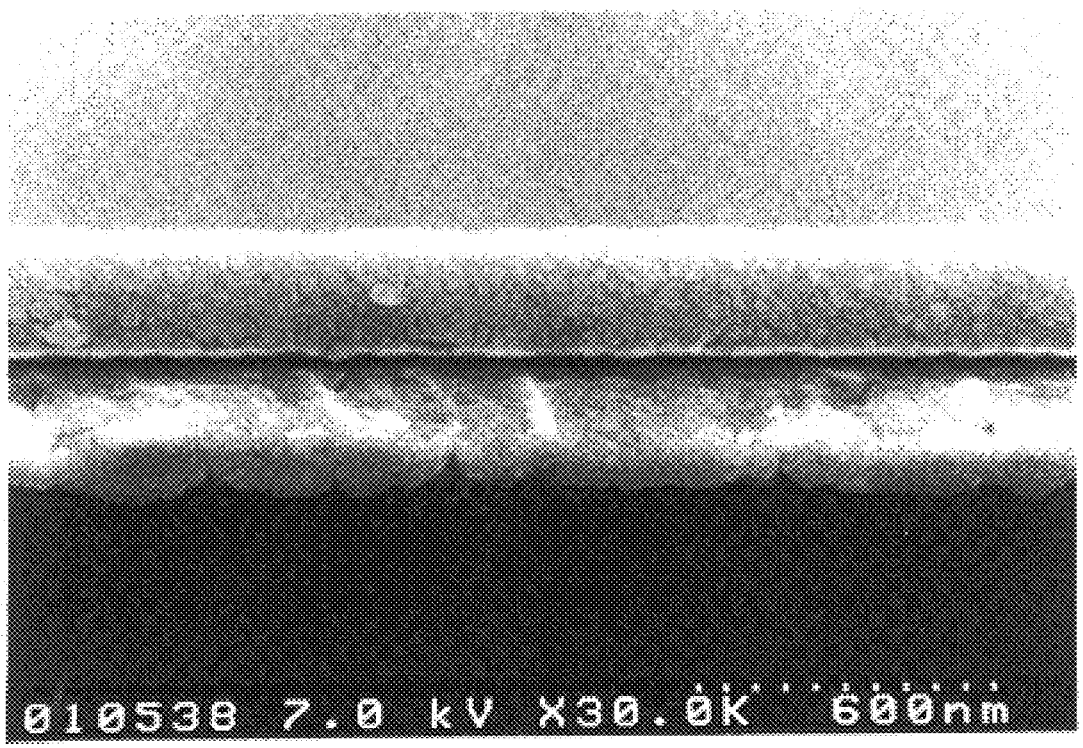
FIG. 5 is a SEM micrograph showing a cross-section of a thin film deposited using the organotitanium precursor of formula 9 at 425° C. in accordance with the ninth embodiment.

The surface shape and cross-section of $TiO_2$ thin film formed by using the compound of Formula 9 were examined by a scanning electron microscopy (SEM). The results show that a thin film having a columnar growth was formed finely and uniformly (FIGS. 4 and 5).

According to the present invention, it is possible to manufacture an organotitanium precursor which is stable in normal atmosphere, easy to handle, has better heating and evaporation stability, and has a superior deposition rate even at relatively low temperatures due to its simple decomposition reaction, and therefore it is possible to provide cost-effective materials for chemical vapor deposition.

While the present invention has been described in detail with exemplary embodiments, it should be understood that various changes, substitutions and modifications are possible thereto without departing from the spirit and scope of the invention as defined by the appended claims.

What is claimed is:

1. A di-nuclear organotitanium precursor of Formula 2

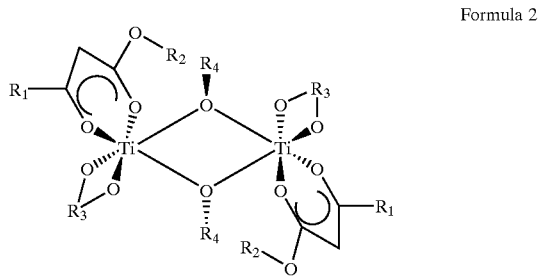

Formula 2 wherein $R_1$ and $R_2$ are each selected from the group consisting of a straight- or branched chain alkyl group each having 1–8 carbon atoms, a cycloalkyl group, a phenyl group and a benzyl group; and $R_3$ is a straight- or branched chain alkylene group having 2–13 carbon atoms, and $R_4$ is a straight chain alkyl group having 1–8 carbon atoms.

2. The organotitanium precursor of claim 1, wherein $R_1$ and $R_2$ are each selected from the group consisting of a straight- or branched chain alkyl group each having 1–5 carbon atoms, a cycloalkyl group, a phenyl group and a benzyl group.

3. The organotitanium precursor of claim 1, wherein $R_3$ is a straight- or branched chain alkylene group having 2–10 carbon atoms.

4. The organotitanium precursor of claim 1, wherein $R_4$ is straight chain alkyl group having 1–6 carbon atoms.

5. A method for manufacturing the organotitanium precursor of Formula 1, comprising the steps of:

(1) reacting a titanium tetraalkoxide, $Ti(OR)_4$, wherein R is a straight- or branched chain alkyl group having 1–4 carbon atoms, with diol of Formula 3;

(2) adding a β-ketoester of Formula 4 to the reaction intermediate resulting in step (1), to form a reaction product; and (3) removing unnecessary by-product ROH and any solvent if used in step 1 from the reaction product and distilling under reduced pressure;

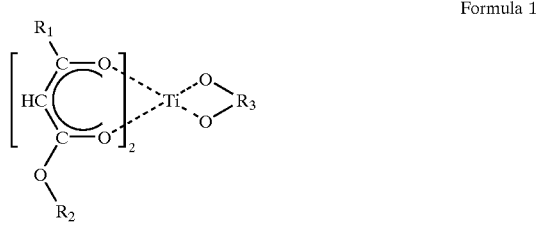

Formula 1 wherein $R_1$ and $R_2$, are each selected from the group consisting of a straight- or branched chain alkyl group each having 1–8 carbon atoms, a cycloalkyl group, a phenyl group and a benzyl group; and $R_3$ is a straight- or branched chain alkylene group having 2–13 carbon atoms;

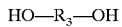   Formula 3 wherein $R_3$ is a straight- or branched chain alkylene group having 2–13 carbon atoms;

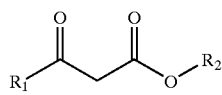

Formula 4 wherein $R_1$ and $R_2$ are each selected from the group consisting of a straight- or branched chain alkyl group each having 1–8 carbon atoms, a cycloalkyl group, a phenyl group and a benzyl group.

6. A method for manufacturing the dimer organotitanium precursor of Formula 2 according to claim 1, comprising the steps of:

(1) reacting a titanium tetraalkoxide, Ti(OR)$_4$, wherein R is a straight- or branched chain alkyl group having 1–4 carbon atoms, with diol of Formula 3;

(2) adding a β-ketoester of Formula 4 to the reaction intermediate resulting in step (1), to form a mono-nuclear reaction product;

(3) removing unnecessary by-product ROH and any solvent if used in step (1) from the reaction product; and (4) distilling under reduced pressure, with the proviso that a step of adding an alcohol, $R_4$OH, where $R_4$ is a straight chain alkyl group having 1–8 carbon atoms, is performed before or after this distilling step to thereby form a di-nuclear reaction product;

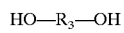

Formula 3 wherein $R_3$ is a straight- or branched chain alkylene group having 2–13 carbon atoms;

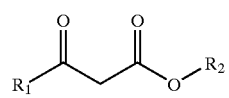

Formula 4 wherein $R_1$ and $R_2$ are each selected from the group consisting of a straight- or branched chain alkyl group each having 1–8 carbon atoms, a cycloalkyl group, a phenyl and a benzyl group.

* * * * *